United States Patent
Bryski et al.

(10) Patent No.: US 9,839,245 B2
(45) Date of Patent: Dec. 12, 2017

(54) EAR WARMING HEADWEAR HAVING RETENTION MEANS FOR SECURING SAME IN AN EAR-COVERING POSITION

(71) Applicants: Lisa Bryski, Winnipeg (CA); Belinda Loschiavo, Winnipeg (CA)

(72) Inventors: Lisa Bryski, Winnipeg (CA); Belinda Loschiavo, Winnipeg (CA)

(*) Notice: Subject to any disclaimer, the term of this patent is extended or adjusted under 35 U.S.C. 154(b) by 235 days.

(21) Appl. No.: 14/726,734

(22) Filed: Jun. 1, 2015

(65) Prior Publication Data
US 2016/0000169 A1 Jan. 7, 2016

Related U.S. Application Data

(60) Provisional application No. 62/021,427, filed on Jul. 7, 2014.

(51) Int. Cl.
*A41D 20/00* (2006.01)
*A61F 11/06* (2006.01)

(52) U.S. Cl.
CPC .............. *A41D 20/00* (2013.01); *A61F 11/06* (2013.01)

(58) Field of Classification Search
CPC ..................................................... A41D 20/00
USPC .......................... 2/181, 183, 209, 9, 15, 206
See application file for complete search history.

(56) References Cited

U.S. PATENT DOCUMENTS

| | | | | | |
|---|---|---|---|---|---|
| 1,242,684 | A | * | 10/1917 | Guinzburg | A42B 1/12 2/68 |
| 2,294,529 | A | * | 9/1942 | Wengen | A42B 1/041 2/172 |
| 3,358,292 | A | * | 12/1967 | Bonk | A42B 1/066 2/172 |
| 5,038,412 | A | * | 8/1991 | Cionni | A41D 20/00 2/171 |
| 5,428,843 | A | * | 7/1995 | Clowers | A42B 1/22 2/183 |
| 6,070,265 | A | * | 6/2000 | Tasbas | A41D 13/11 128/858 |
| 2002/0120976 | A1 | * | 9/2002 | Cannings | A45D 8/36 2/171 |
| 2012/0222193 | A1 | * | 9/2012 | Terrell | A41D 20/00 2/181 |

* cited by examiner

*Primary Examiner* — Katherine Moran
(74) *Attorney, Agent, or Firm* — Kyle R Satterthwaite; Ryan W Dupuis; Ade & Company Inc.

(57) ABSTRACT

A thin athletic headband, tuque or knit cap has selective areas of extra padding and elastic bands extending around the ears at a position thereunder. The extra thickness or layering at the ear areas provides increased ear protection in cold and/or windy weather, while the elastic provides an area of increased headband tension below the ears to block sliding of the headwear upwardly out of the proper ear-covering position. This headwear can be used alone or under protective headgear, for example beneath a hockey helmet.

14 Claims, 2 Drawing Sheets

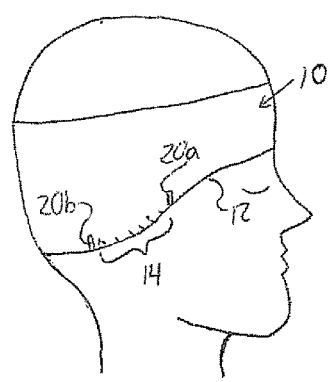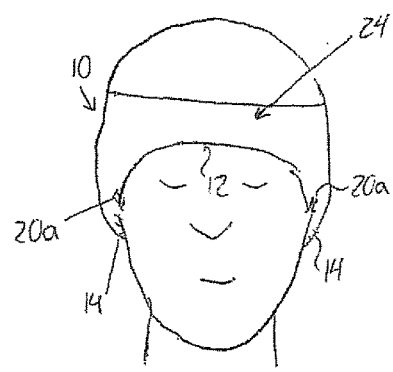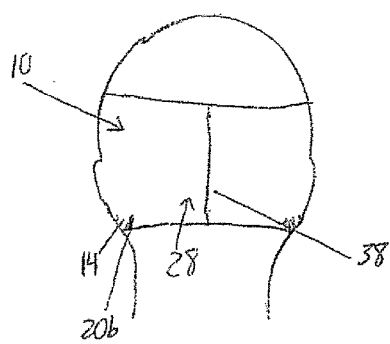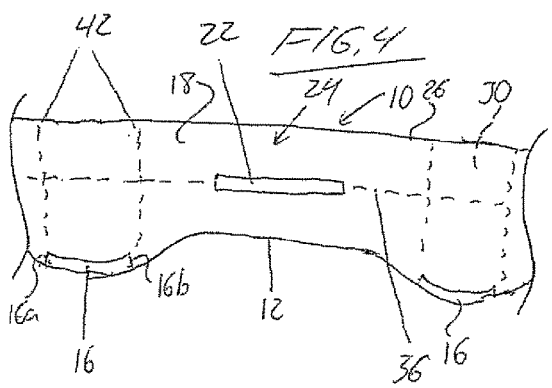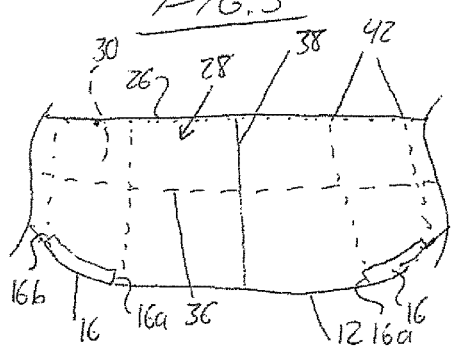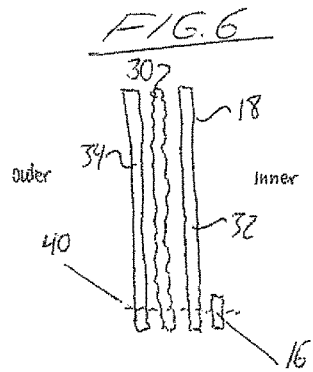

EAR WARMING HEADWEAR HAVING RETENTION MEANS FOR SECURING SAME IN AN EAR-COVERING POSITION

CROSS REFERENCE TO RELATED APPLICATIONS

This application claims benefit under 35 U.S.C. 119(e) of Provisional Application Ser. No. 62/021,427, filed Jul. 7, 2014.

FIELD OF THE INVENTION

The present invention relates to a headband with ear protection for use in general by a person exposed to cold and/or windy conditions, and more particularly to headwear with a circumferential band incorporating extra elasticity below or behind the earlobes in order to use the ear as an anchoring feature to hook the headband in place and block sliding thereof upwardly from its ear-covering position. This headwear can be used alone or in conjunction with protective headgear used for sport or workplace safety.

BACKGROUND

When people are active in cold and/or windy weather, they use protective outerwear such as hats, headbands, earmuffs, and other outerwear for the purpose of keeping their ears from being exposed to the elements. These outerwear ear protectors may be used alone or under different protective headgear, such as helmets used for sport or work related safety.

Many helmets, especially those used in hockey, bicycling, and work safety, do not fully cover the ears leaving the ears susceptible to harsh weather. Some helmets are equipped with removable ear pads, but these are helmet specific and can neither be used alone nor be easily interchangeable with other helmets.

Different problems can be encountered depending on the activity performed or the outerwear used. When used alone, a headband or hat no matter the thickness will still leave a gap between the back of the ear and the head. As well during activity, the headband or hat will ride up exposing portions of, or the entire, ear to uncomfortable weather. Further, the person is often adjusting the head wear causing distraction and frustration which leads to poor performance.

Many concerns arise when insulating ear wear is used under helmets. Due to the requirement that protective headgear such as helmets fit snugly during activity for maximum safety, insulated ear wear such as earmuffs and thicker hats or headbands do not fit under helmets. Thin, wicking headbands fit under helmets and help with forehead perspiration, but are limited by the following difficulties. Thin headbands do not have extra ear insulation, do not cover the gap between the ear and the head, and also ride up increasing ear exposure to inclement weather.

When used under helmets to provide increased ear coverage, balaclavas also have concerns. Balaclavas do not readily move with a person's head and neck movements thus coming out of alignment, restricting the person's field of vision and requiring constant adjustment. If the balaclava is thin enough to fit under various helmets and provide coverage for the gap between the ear and head, it still lacks thick material covering the ears to provide optimum wind and cold protection.

The optimal solution to these concerns is ear protection that can be used alone or is easily interchangeable between helmets of different sizes, styles, brands and configurations. This ear protection should be made of material that is thin enough to be comfortably worn under a closely fitted helmet, but has increased protection around the ear area. This protection is in the form of thicker material covering the ear zone of the head, as well as tension provided by an elastic strip that allows a snug but comfortable fit around the ear. This combination of protection will substantially increase shielding of the ear from heat loss and wind discomfort.

SUMMARY OF THE INVENTION

According to one aspect of the invention there is provided ear-warming headwear with means for preventing displacement thereof from a position covering both ears of a wearer's head, said ear-warming headwear comprising:

an ear-covering member comprising a circumferential band for use in a worn position circumscribing said wearer's head and overlying both ears thereof;

two elastic members attached to the circumferential band adjacent a bottom edge thereof at positions lying generally opposite one another across a space delimited by the circumferential band, in order to hold the ear-covering member in a snug fit against the wearer's head below the ears of the wearer's head or behind earlobes thereof, whereby the snug fit cooperates with the ears to block sliding of the bottom edge of the circumferential band upwardly past either earlobe, thereby blocking upward displacement of the circumferential band out of the worn position.

The ear-covering member may be a headband that leaves a crown of the wearer's head exposed in the worn position.

The ear-covering member may be a cap that includes a crown portion attached to and closing over the circumferential band to cover a crown of the wearer's head in the worn position.

Preferably the ear-covering member has two discrete ear-covering areas residing at the same positions around the circumferential band as the elastic members, the discrete ear-covering area having greater thickness than other areas of the circumferential band to provide greater thermal protection at the ears of the wearer's head.

Preferably the discrete ear-covering areas of greater thickness span substantially a full width of the circumferential band from the bottom edge thereof to an opposing top edge thereof.

Preferably the discrete ear-covering areas of the circumferential band each have a multi-layer construction.

Preferably the multi-layer construction of the discrete ear-covering areas of the circumferential band comprise a greater number of layers than the other areas of the circumferential band.

Preferably the multi-layer construction of the discrete ear-covering areas of the circumferential band comprise an inner layer of moisture wicking material that resides over the ears of the wearer's head at said discrete ear-covering areas, and an insulating layer overlying the inner layer and comprising a different material of greater thermally insulation value than the moisture wicking material of said inner layer.

Preferably the inner layer of moisture wicking material spans around the entire circumferential band.

The circumferential band may have an outer layer overlying the insulation layer to face outwardly away from the wearer's head during use.

The inner and outer layer may comprise a common piece of the moisture wicking material that is folded around the insulation layer and seamed together to fully enclose the insulation layer.

Preferably the outer layer spans around the entire circumferential band.

The elastic members may be disposed internally of the circumferential band between adjacent layers thereof.

Alternatively, the elastic members may be attached to an interior surface of the circumferential band that faces toward, and is exposed to, the wearer's head during use.

A grip member may be attached to an inner side of the circumferential band that faces toward, and is exposed to, the wearer's head during use, the grip member being positioned at an intermediate area around the circumferential band between the elastic members and having a greater frictional coefficient than said inner side of the circumferential band in order to frictionally grip the forehead of the wearer's head to further prevent displacement of the circumferential band.

According to a second aspect of the invention, there is provided a method of producing ear-warming headwear comprising:

providing an ear-covering member comprising a band for use in a worn position circumscribing a wearer's head and overlying both ears thereof; and attaching first and second elastic members to the circumferential band at positions adjacent to, and spaced apart along, a bottom edge thereof at spaced apart positions therealong that will reside generally opposite one another in the worn position so as to respectively reside near a bottom of each ear of the wearer's head;

wherein the step of attaching of the elastic members comprises attaching opposing ends of each elastic member to the circumferential band while said elastic member is in a stretched state of greater tension than the band so that the elastic members create first and second areas of the band that have greater tension than other areas of the band when worn, thereby providing a snug fit of the band below and behind each earlobe of the wearer in order to block sliding of the bottom edge of the band upwardly past the earlobes, which prevents upward displacement of the band out of the worn position overlying the ears.

According to a third aspect of the invention, there is provided a method of preventing displacement of ear-warming headwear out of a worn position overlying both ears of a wearer's head, the method comprising placing a circumferential band in the worn position, including positioning of the circumferential band in a manner placing two areas of said band that have greater circumferential tension than other areas of said circumferential band at respective positions below or behind the earlobes of the wearer's head to provide a snug fit of said circumferential band against the wearer's head below or behind the earlobes, whereby the snug fit below or behind the earlobes cooperates with the ears to block sliding of the areas of greater circumferential tension upwardly past the earlobes, thereby blocking upward displacement of the circumferential band upwardly out of the worn position.

BRIEF DESCRIPTION OF THE DRAWINGS

Preferred embodiments of the invention will now be described in conjunction with the accompanying drawings in which:

FIG. 1 depicts a right side view of a first embodiment headband of the present invention during use in a position worn circumferentially around the head to overlie and protect both of the user's ears. The unillustrated left side view is a mirror image of the right side view.

FIG. 2 depicts a frontal view of the headband of FIG. 1 during use.

FIG. 3 depicts a back view of the headband of FIG. 1 during use.

FIG. 4 depicts a plan view of the first embodiment's ear protection areas and front section of the headband as viewed from the interior thereof, as would be seen if laid out flat with a rear section of the headband cut away.

FIG. 5 depicts a plan view of the first embodiment's ear protection area and back section of headband as viewed from the interior thereof, as would be seen if laid out flat with the front section of the headband cut away.

FIG. 6 depicts an exploded cross-sectional view of a multi-layer construction of each ear protection area of the first embodiment headband.

In the drawings like characters of reference indicate corresponding parts in the different figures.

DETAILED DESCRIPTION

Figure 7:
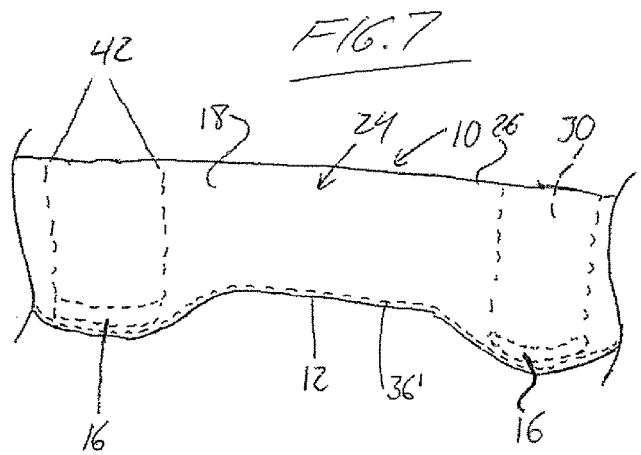
FIGS. 7 through 9 are similar to FIGS. 4 through 6, but show a second embodiment that differs in the particular placement of elastic strips within a multi-layered construction of the headband, and in the location of a seam at which inner and outer layers of the headband are sewn together.

FIGS. 1 to 3 show a first embodiment headband of the present invention in use on a wearer. While in use, the headband has a similar outward appearance as a conventional ear-warming headband, as it includes a circumferential band 10 in the form of a stretchable closed loop configuration whose natural unstretched condition has a circumferential span less than that of the wearer's head, whereby the headband is adorned by stretching the band 10 to a diameter slidable downwardly over the crown of the user's head into a worn position circumscribing the head and overlying the ears. In this worn position, the headband passes across the forehead, rearwardly from the temples over both of the wearer's ears, and around the back of the head. The bias of the headband fabric back towards its original unstretched condition provides some frictional hold through its contact with the wearer, but as described above, this conventional securing means is often insufficient, and often allows conventional headbands to shift out of the desired position in which they maintaining full coverage and thermal protection of the ears. Accordingly, the present invention adds unique additional features to the headband to help secure it in the proper position, and maintain this position, even throughout strenuous movement and activity by the wearer.

With reference to FIG. 1, the bottom edge 12 of the headband can be seen to have a puckered area 14 at which it is slightly bunched up over a short fraction of the headband's circumference around the head, specifically at an area thereof residing beneath the ear on the illustrated side of the wearer's head. Likewise, a matching puckered area also resides below the ear on the other side of the head. This puckering occurs as a result of a greater circumferential tension provided in this area 14 of the headband than at the remaining areas of the headband, whereby the bottom edge 12 of the headband fits snugly against the side of the user's head just below the earlobe.

As a result, any tendency for the headband to ride upwardly out of its worn position fully covering the ear is blocked by cooperation of this greater-tensioned area of the headband with the ear. That is, this tensioned region of the headband spanning under the ear over a fraction of the headband's bottom edge 12 effectively hooks around the bottom of the ear, thereby catching against underside and back of the ear behind the lobe in order to anchor the headband in place and prevent upward sliding of the headband's bottom edge 12 up past the earlobe. Accordingly, upward sliding of the headband from its proper ear-covering position is prevented.

Turning to FIGS. 4 and 5, to create these two higher-tension areas 14 of the headband 10, two strips of elastic band 16 are attached to the interior surface 18 of the headband just above the bottom edge 12 of the headband at spaced apart positions around the circumference thereof. During fabrication of the headwear, with the headband at its default size in an unstretched state, each elastic strip 16 is sewn to the headband 12 at its two ends 16a, 16b while being held in a stretched condition. This way, once the elastic strip 16 is sewn in place and released from its stretched condition, the resiliency of the elastic will act to draw the two ends 16a, 16b of the elastic strip 16 toward one another. Since these two ends 16a, 16b are respectively sewn to spaced-apart points along the bottom edge 12 of the headband, this resilient action of the elastic strip 16 will likewise draw these two points of the headband's bottom edge 12 toward one another, thereby causing the bunched up or puckered area 14 shown in FIG. 1.

When the headband is stretched over the crown of the wearer's head, this stretches the elastic strips along with it while the headband is drawn downwardly into the worn position that fully covers the ears and places the two elastic strips 16 just below the ears. Because the elastic strips 16 were attached to the headband in a state of greater stretch, upon releasing the stretched state of the headband, the length of each elastic strip contracts even further, back toward its default, naturally-biased unstretched state. This elastic contraction of each elastic pulls its two headband-connected ends toward one another. Accordingly, the headband is tensioned tighter around the wearer's head at this elastic-equipped area 14 of its lower edge beneath the respective ear, thus drawing this edge-adjacent portion of the headband inwardly past the ear-covering portion of the headband and into abutment against the side of the head just below the ear. Any upward pulling or riding of the headband will cause this higher-tensioned area of the headband's lower edge 12 to ride up into the space behind the earlobe (i.e. between the earlobe and the user's head at the area of the head normally concealed by the earlobe), thus hooking this area of the headband's lower edge 12 around the earlobe and up against the portion of the ear that juts out from the cranium. The bottom edge 12 of the headband is thus blocked from riding further upward past this point, thereby blocking withdrawal of the headband from the proper worn position over the ear. With ear-based anchoring function occurring at both sides of the wearer's head through cooperation of each elastic strip with a respective ear, the headband is thus well secured in the proper position on the wearer's head. In addition, this snug fitting of the elastic-equipped area of the headband against the wearer's head where the bottom edge 12 of the headband passes rearwardly beneath the ear closes up the gap between the headband and wearer's head that normally occurs at the back of the ear with a conventional headband.

As mentioned above, despite this extra position-retaining and gap closing functionality provided by the headband of the present invention, the outward appearance of the headband may remain substantially unchanged from a conventional headband, with the small amount of folding or bunching at the puckered area 14 below each ear, and possibly the presence of an outwardly visible seam of stitching 20a, 20b at each end of the elastic strips 16, being fairly minor and substantially unnoticeable.

With reference to FIG. 4, further anchoring of the headband 10 in the proper position may be performed by the addition of a piece 22 of silicone or other grip material that has a greater coefficient of friction with the wearer's skin than the interior surface of the band 12 itself. This piece 22 is sewn or otherwise attached to the interior surface of the headband that faces toward and is exposed to the user's head when the headwear is adorned, for example on the front section 24 of the headband at a central location between the two ear-covering areas thereof, whereby this grip piece 22 will be placed in contact with the skin of the wearer's forehead when the headband is worn. This provides an extra resistance to riding-up of the headband at the forehead area, and also resists circumferential displacement of the headband around the wearer's head. As shown, the grip piece 22 may take the form of an elongated strip whose length lies in the circumferential direction of the headband 12 at a generally central location between the top and bottom edges 26, 12 thereof. This grip piece 22 is optional, as demonstrated by the second embodiment shown in FIG. 7, which lacks a grip piece 22 on the interior surface of the headband.

As shown, the width of the headband measured between the top and bottom edges 26, 12 thereof may be greater at the ear-covering areas (where the elastic strips 16 are located) than at the front section 24 that covers the wearer's forehead, thereby ensuring full coverage of the wearer's ears while minimizing potential interference with the wearer's vision at the brow area. In the illustrated embodiments, the bottom edge 12 of the headband thus slopes downwardly away from the top edge 26 at the areas reaching rearwardly from the wearer's temples toward the ears and back of the head. As shown, the greater width present at the ear-covering areas may be maintained across the rear section 28 of the headband that overlies the back of the user's head. Alternatively, the headband width measured between the top and bottom edges 26, 12 may remain the same throughout the circumference of the headband.

With reference to FIGS. 4 to 6, for optimal thermal protection of the ears, the two ear-covering areas of the headband may feature a multi-material, multi-layer construction, for example featuring an insulation layer 30 sandwiched between inner and outer cover layers 32, 34 that form a skin or shell of the headband. The cover layers 32, 34 may be made of a moisture wicking material, whereby the inner cover layer 32 defining the interior surface 18 of the headband will draw sweat away from the user's skin during use. The insulation layer 30 can be made of fleece or other material of greater thermal insulation value than the cover layers. Making the inner and outer layers of the same material allows optional use of a single common piece of this material to form both of these cover layers, thereby reducing the number of seams required to fabricate the headband.

Figure 8:
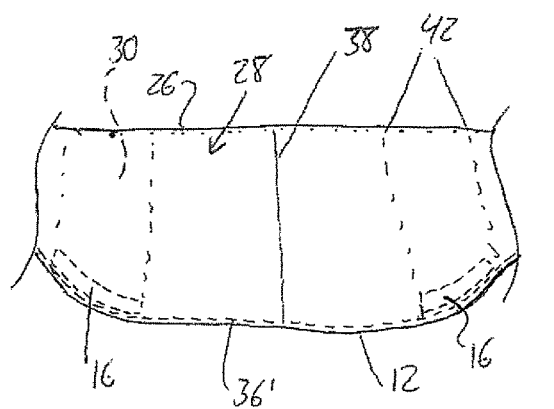

In the first embodiment shown in FIGS. 4 and 5, this single piece of material is wrapped around the top and bottom edges of the insulation material 30 and sewn together at overlapped edges of this wrapped piece of cover material at a central longitudinal seam 36 running parallel to the top edge 26 of the headband on the inner side 18 thereof, as shown in FIGS. 4 and 5. In the second embodiment shown in FIGS. 7 and 8, the overlapped edges of the single piece of material instead overlap one another at or near the bottom edge 12 of the headband, whereby the longitudinal seam 36' resides at or adjacent to, and runs along, the bottom edge 12 of the headband instead of residing at a central or intermediate area between the top and bottom edges of the headband.

As shown in FIGS. 3 and 5, the closed-loop form of the finished headband can be obtained by sewing together two ends of an originally double ended strip to form at a widthwise seam 38 at the back section 28 of headband at a central position between the two ear covering areas.

Figure 9:
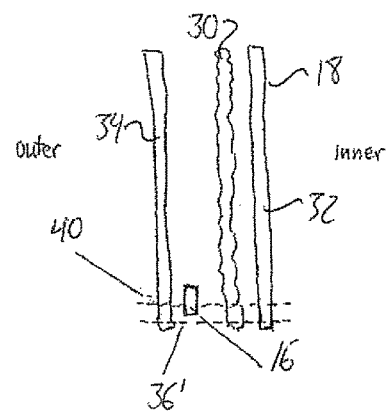

FIG. 6 shows attachment of one of the elastic strips 16 to the ear-covering area of the headband by sewing of each of it ends to the interior surface 18 defined by the inner layer 32 of the multi-layer headband construction, as shown schematically by schematic stitching 40. In other embodiments, instead of having the elastic strip 16 attached at the exposed interior surface 18 of the headband, it may alternatively be incorporated internally of the headband between adjacent layers thereof. For example, the second embodiment shown in FIG. 9 features placement of the elastic strips 16 between the outer layer 34 and the insulation layer 30.

As an alternative to the multi-fabric construction described above with moisture wicking cover layers and an intermediate insulation layer, other embodiments may employ other constructions of varying layers and fabrics. In one such embodiment, only two inner and outer layers of fleece or other fabric are employed without the presence of a separate intermediate insulation layer between them at the ear-covering portions of the headband. In such an embodiment, the elastics can again either situated at the interior surface 18 of the headband (like in the first embodiment), or contained between the inner and outer layers (like in the second embodiment). Using fleece or another fabric with an inherent subtle gripping function due to frictional properties of the material helps prevent displacement of the circumference band from its worn position, and therefore further reduces the need for the optional grip strip 22 shown in the first embodiment.

In the illustrated embodiments, the insulation layer 30 is included only at the two ear-covering areas. Accordingly, two separate and discrete insulation pieces 30 are used, each residing at a respective position around the headband 10 that matches that of the respective one of the two elastic strips 16. Each insulation piece 30 spans substantially the full width of the headband at the respective ear-covering area thereof, reaching fully from the bottom edge 12 of the headband to the top edge 26 thereof so as to ensure full coverage of the respective ear with the thermal insulation material. The lack of insulation material at the remaining front and rear sections of the headband gives these sections a thinner construction of fewer layers (for example, solely the folded-over piece of cover material that may define both the inner and outer layers 32, 34). This minimizes interference of the headband with fitting of a hockey helmet or other protective headwear over the headband, while providing optimal thermal protection of the ears, which are typically left exposed by such protective headwear. To prevent shifting of the insulation material 30 circumferentially inside the shell layers, FIGS. 4 and 5 show widthwise seams 42 sewn along the widthwise edges of the insulation pieces 30 from the top edge 26 of the headband down to the bottom edge 12 thereof.

One embodiment intended for wearing by adults has a headband length or circumference of 23-inches, of which 9-inches is spanned by the front forehead section, 4-inches is spanned by the rear section and the remaining 10-inches is spanned in equal halves (i.e. 5-inches each) by the two ear-covering areas; the headband width is 2.5 inches at the front forehead section, and 4-inches at the ear-covering areas and the rear section; each elastic strip is 3-inches long and 0.25-inch wide in its unstretched state, and is sewn to the headband while stretched to a 5-inch length; the grip piece is 5-inches long and centered on the 9-inch length of the front forehead section. It will be appreciated that these dimensions are presented as examples only, and are not intended to limit the invention to this particular size.

One junior-sized embodiment intended for wearing by younger users has a headband length or circumference of 20-inches, of which 8-inches is spanned by the front forehead section, 4-inches is spanned by the rear section and the remaining 8-inches is spanned in equal halves (i.e. 4-inches each) by the two ear-covering areas; the headband width is 2-inches at the front forehead section, 3.5-inches at the ear-covering areas and the rear section; each elastic strip is 2.5-inches long and 0.25-inch wide in its unstretched state, and is sewn to the headband while stretched to a 4-inch length; the grip piece is 4-inches long and centered on the 8-inch length of the front forehead section. Again, it will be appreciated that these dimensions are presented as examples only, and are not intended to limit the invention to this particular size.

Although the headwear of the illustrated embodiments is configured as a headband that leaves the crown of the head exposed during use, it will be appreciated that the same provision of tension-increasing elastics below the ears to provide improved retention means and coverage, and/or increased thickness or layering at ear-covering areas, can be used in other headwear, for example a tuque or knit cap that additionally features a cap or crown portion that spans over the headband from the top edge thereof to cover the crown of the wearer's head. As in a traditional tuque or cap construction, this cap portion may be an integral extension of the 'band' area that circumscribes the forehead, sides and back of the head in a position covering the wearer's ears. Alternatively, a separate cap portion could be sewn or otherwise attached to an initially separate headband, for example like that illustrated and described herein above.

Since various modifications can be made in my invention as herein above described, and many apparently widely different embodiments of same made within the scope of the claims without departure from such scope, it is intended that all matter contained in the accompanying specification shall be interpreted as illustrative only and not in a limiting sense.

The invention claimed is:

1. Ear-warming headwear with means for preventing displacement thereof from a position covering both ears of a wearer's head, said ear-warming headwear comprising:

an ear-covering member comprising a circumferential band for use in a worn position circumscribing said wearer's head and overlying both ears thereof;

two elastic members attached to the circumferential band adjacent a bottom edge thereof at positions lying generally opposite one another across a space delimited by the circumferential band, each elastic member having two ends which are sewn to the circumferential band at two respective points thereon, and said each elastic member also having a resiliency that draws said two ends of the elastic member toward one another and likewise draws the two points of the circumferential band toward one another, which creates a puckered area of the circumferential band where the circumferential band is bunched up between the two points and a circumferential tension of said circumferential band is greater than at remaining areas of said circumferential band other than said puckered areas, whereby the bottom edge of the circumferential band fits snugly against sides of the wearer's head just below earlobes thereof, in the worn position;

wherein the ear-covering member has two discrete ear-covering areas residing at the same positions around the circumferential band as the elastic members, and the discrete ear-covering area have greater thickness than other areas of the circumferential band to provide greater thermal protection at the ears of the wearer's head.

2. The ear-warming headwear of claim 1 wherein the ear-covering member is a headband that leaves a crown of the wearer's head exposed in the worn position.

3. The ear-warming headwear of claim 1 wherein the ear-covering member is a headband that leaves a crown of the wearers head exposed in the worn position, and the discrete ear-covering areas of greater thickness span substantially a full width of the circumferential band from the bottom edge thereof to an opposing top edge thereof.

4. The ear-warming headwear of claim 1 wherein the discrete ear-covering areas of the circumferential band each have a multi-layer construction.

5. The ear-warming headwear of claim 4 wherein the multi-layer construction of the discrete ear-covering areas of the circumferential band comprises a greater number of layers than the other areas of the circumferential band.

6. The ear-warming headwear of claim 4 wherein the multi-layer construction of the discrete ear-covering areas of the circumferential band comprise an inner layer of moisture wicking material that resides over the ears of the wearers head at said discrete ear-covering areas, and an insulating layer overlying the inner layer and comprising a different material of greater thermally insulation value than the moisture wicking material of said inner layer.

7. The ear-warming headwear of claim 6 wherein the inner layer of moisture wicking material spans around the entire circumferential band.

8. The ear-warming headwear of claim 6 wherein the circumferential band comprises an outer layer overlying the insulation layer to face outwardly away from the wearers head during use.

9. The ear-warming headwear of claim 8 wherein the inner and outer layer comprise a common piece of the moisture wicking material folded around the insulation layer and seamed together to fully enclose the insulation layer.

10. The ear-warming headwear of claim 8 wherein the outer layer spans around the entire circumferential band.

11. The ear-warming headwear of claim 1 wherein the elastic members are attached to an inner surface of the circumferential band that faces toward, and is exposed to, the wearer's head during use.

12. The ear-warming headwear of claim 1 wherein the elastic members are disposed internally of the circumferential band between adjacent layers thereof.

13. The ear-warming headwear of claim 1 comprising a grip member attached to an inner side of the circumferential band that faces toward, and is exposed to, the wearer's head during use, the grip member being positioned at an intermediate area around the circumferential band between the elastic members and having a greater frictional coefficient than said inner side of the circumferential band in order to frictionally grip the forehead of the wearer's head to further prevent displacement of the circumferential band.

14. Ear-warming headwear with means for preventing displacement thereof from a position covering both ears of a wearer's head, said ear-warming headwear comprising:

an ear-covering member comprising a circumferential band for use in a worn position circumscribing said wearer's head and overlying both ears thereof;

two elastic members attached to the circumferential band adjacent a bottom edge thereof at positions lying generally opposite one another across a space delimited by the circumferential band, each elastic member having two ends which are sewn to the circumferential band at two respective points thereon, and said each elastic member also having a resiliency that draws said two ends of the elastic member toward one another and likewise draws the two points of the circumferential band toward one another, which creates a puckered area of the circumferential band where the circumferential band is bunched up between the two points and a circumferential tension of said circumferential band is greater than at remaining areas thereof other than said puckered areas, whereby the bottom edge of the circumferential band fits snugly against sides of the wearer's head just below earlobes thereof, in the worn position;

wherein the elastic members are disposed internally of the circumferential band between adjacent layers thereof.

\* \* \* \* \*